(12) United States Patent
Wen et al.

(10) Patent No.: US 8,840,767 B2
(45) Date of Patent: Sep. 23, 2014

(54) LOW MAINTENANCE REFERENCE ELECTRODE FOR ELECTROCHEMICAL MEASUREMENTS

(75) Inventors: Xiaowen Wen, Lexington, MA (US); Hyoungsik Yim, North Chelmsford, MA (US); Lori Hrdy, Salem, MA (US); Dawood Bhaijee, Burlington, MA (US)

(73) Assignee: Thermo Fisher Scientific, Inc., Beverly, MA (US)

( * ) Notice: Subject to any disclaimer, the term of this patent is extended or adjusted under 35 U.S.C. 154(b) by 0 days.

(21) Appl. No.: 13/455,727

(22) Filed: Apr. 25, 2012

(65) Prior Publication Data

US 2012/0205245 A1  Aug. 16, 2012

Related U.S. Application Data

(63) Continuation of application No. 12/541,476, filed on Aug. 14, 2009, now Pat. No. 8,172,999.

(60) Provisional application No. 61/088,888, filed on Aug. 14, 2008.

(51) Int. Cl.
*G01N 27/30* (2006.01)
*G01N 27/36* (2006.01)
*G01N 27/403* (2006.01)
*G01N 33/49* (2006.01)
*G01N 33/18* (2006.01)

(52) U.S. Cl.
CPC ............ *G01N 27/4035* (2013.01); *G01N 33/49* (2013.01); *G01N 27/301* (2013.01); *G01N 33/18* (2013.01)

USPC ........... 204/435; 204/433; 204/416; 204/406; 422/502; 422/503; 422/507

(58) Field of Classification Search
CPC ..................................................... G01N 27/301
USPC .......... 204/433, 435, 416, 408; 422/502, 503, 422/507

See application file for complete search history.

(56) References Cited

U.S. PATENT DOCUMENTS

| | | | |
|---|---|---|---|
| 3,915,829 A | 10/1975 | Krebs | |
| 4,406,766 A | 9/1983 | MacDonald | |
| 4,495,052 A | 1/1985 | Brezinski | |
| 4,959,138 A | 9/1990 | Brinkman et al. | |
| 5,264,722 A * | 11/1993 | Tonucci et al. | 257/443 |
| 6,468,408 B2 * | 10/2002 | Thrier et al. | 204/435 |
| 6,616,821 B2 * | 9/2003 | Broadley et al. | 204/435 |
| 7,005,049 B2 * | 2/2006 | Broadley et al. | 204/416 |
| 7,025,871 B2 * | 4/2006 | Broadley et al. | 205/793 |

(Continued)

FOREIGN PATENT DOCUMENTS

WO  WO 2008090403 A1 *  7/2008  ............. G01N 27/30

*Primary Examiner* — Luan Van
*Assistant Examiner* — Steven Rosenwald
(74) *Attorney, Agent, or Firm* — Gordon Stewart

(57) ABSTRACT

A low maintenance reference electrode has a liquid junction body with a multiplicity of micron-sized capillary channels extending through the body for transporting electrolyte to a test solution. A viscosity-increasing agent thickens the electrolyte to limit its flow to a rate on the order of microliters/day so that a few milliliters of electrolyte suffice to provide an extended electrode life.

12 Claims, 1 Drawing Sheet

(56) References Cited

U.S. PATENT DOCUMENTS

| | | |
|---|---|---|
| 7,344,627 B2 | 3/2008 | Broadley et al. |
| 7,459,066 B2 * | 12/2008 | Broadley et al. .............. 204/435 |
| 8,048,278 B2 * | 11/2011 | Broadley et al. .............. 204/435 |
| 8,172,999 B2 * | 5/2012 | Wen et al. ..................... 204/435 |
| 2002/0065332 A1 | 5/2002 | Choi et al. |
| 2004/0231984 A1 | 11/2004 | Lauks et al. |
| 2008/0099336 A1 * | 5/2008 | Broadley et al. .............. 204/435 |
| 2008/0275653 A1 * | 11/2008 | Cypes et al. .................. 702/24 |

* cited by examiner

LOW MAINTENANCE REFERENCE ELECTRODE FOR ELECTROCHEMICAL MEASUREMENTS

CROSS-REFERENCE TO RELATED APPLICATIONS

The present application is a continuation of U.S. patent application Ser. No. 12/541,476, filed on Aug. 14, 2009, which claims the benefit of U.S. Provisional Patent Application Ser. No. 61/088,888, filed on Aug. 14, 2008, by Xiaowen Wen et al. for LOW MAINTENANCE ELECTRODE, which are hereby incorporated by reference.

BACKGROUND OF THE INVENTION

1. Field of the Invention

The invention relates to electrodes for measurement of ion activity in solution and, more particularly, to low-maintenance reference electrodes for such purposes.

2. Background Information

The measurement of ion activity in solution has wide-ranging application in both science and industry. In medicine, the concentration of various ions in the blood and other body fluids can be an important indicator of a patient's health. In industry, knowledge of the presence or absence or various ion species, and their concentrations, may be critical to various processes. In examining water quality, ion concentration measurements are often critical to assessing the viability of water resources.

Electrode-based ion measurement systems typically comprise a measuring electrode (often referred to as a sensing or test electrode) which is responsive to the particular ion whose concentration in solution is to be measured and a reference electrode which provides a stable junction potential against which the measuring electrode potential is to be compared. The sensing electrode typically is connected to the solution being tested by an ion-selective material that is preferential for the ion to be measured; the reference electrode is typically connected to the solution by an electrically conductive "bridge" or "junction" through which electrically conductive material ("filling solution" or "reference solution") travels to form a circuit for measuring current flow. These junctions take a variety of forms.

One common form of junction is a porous material such as a ceramic frit which allows an electrically conductive internal reference solution to seep out from the electrode and into the solution being tested to thereby establish an electrically conductive path between the electrode and the solution. An example of such a junction is shown in U.S. Pat. No. 4,495,052, issued Jan. 22, 1985 to Brezinski. Such junctions are susceptible fouling and thus must periodically be removed from service for cleaning or even replacement.

Another form of junction is shown in U.S. Pat. No. 3,915,829 issued Oct. 28, 1975 to Krebs which discloses a polycarbonate sheet having a multiplicity of sub-micron channels formed in it by ion bombardment. This type of electrode relies on a continuous flow of electrolyte reference solution through the junction and into the test solution to prevent fouling. This, of course, eventually depletes the reference solution. A similar form of junction is described in U.S. Pat. No. 7,344,627 issued Mar. 18, 2008 to Broadley et al. (as well as earlier patents in this same patent family) which disclose a polycarbonate sheet having a multiplicity of nano-sized channels formed in it by ion bombardment. A positive pressure is applied to the electrolyte reference solution in order to establish a flow of sufficient intensity to prevent fouling.

Still another form of junction is the so-called "Hamilton pH sensor" which uses a single channel or pore to connect the internal reference solution to the test solution. To the same effect see also U.S. Pat. No. 4,959,138 to Brinkmann et al.

SUMMARY OF THE INVENTION

In accordance with the present invention, we provide an electrochemical reference electrode having an electrolyte junction that is resistant to fouling yet is long lasting without the need for intermediate maintenance. The junction comprises a multibore body, preferably of from 0.1 to 1 inch in length, and having a multiplicity of small-bore capillary tubes or channels ("capillaries") extending through it along the length of the body generally parallel to each other. The capillaries may be from 10 to 1000 in number, with the inner diameter of each capillary being from 1 to 150 microns. The length-to-diameter ratio of the capillary body is thus much greaer than one, ranging from on the order of ten (for a body length of 0.1 inch and a capillary bore diameter of 150 microns) to on the order of $10^4$ (for a body length of 1 inch and a capillary bore diameter of 1 micron).

The junction material is preferably glass, since this is a naturally wetting material and need not be treated to establish hydrophilicity. The body may be formed by fusing a multiplicity of glass tubes together into a composite bundle, or may be formed by drilling a solid glass body, or by other means. It will be understood, however, that other materials such as ceramics, metal, plastic, hydrophilic hollow fiber, and the like, may also be used. In a proposed commercial embodiment, .we have used a junction body of hexagonal shape, approximately 0.4 inches in length, having 37 glass capillary tubes aligned parallel to each other, and each capillary of approximately 100 microns in diameter.

The junction of the invention is used in connection with a reference solution that has been thickened by a viscosity-increasing agent or, as appropriate, gelled, to limit flow of reference solution out of the electrode and into the test solution. By this means, an electrode having from eight to ten milliliters of reference solution can last on the order of a year without maintenance. It is particularly suited for commercial applications such as water testing and the like, where the electrode is used in the field or other commercial setting and does not receive the more gentle handling characteristic of laboratory usage. It is especially suited for low ionic strength applications such as water quality testing.

The electrode of the present invention enables the maintenance of a relatively constant reference potential for test measurements. It provides a sufficient net dominant flow of reference solution to the test solution to maintain the desired junction potential, yet not so great as to deplete the reference solution and require its replenishment in a short period of time.

The reference solution may advantageously be composed of redox couples such as iodine/iodide to work with potentiometric redox electrodes, such as the Ross® electrode which uses an iodide/iodine filling solution and a platinum electrode to provide a highly temperature-stable reference voltage; or can be composed of halide salts such as potassium chloride to work with silver-silver halide electrodes. These all can be saturated or over saturated with an equally transferent salt such as potassium chloride and potassium nitrate; this enhances the conductivity of the electrode and extends its lifetime.

The reference solution is thickened by dissolving polymers such as polyacrylamide and cellulose, or by mixing in inert filler materials such as silica based Cab-o-sil. In the case of a double-junction reference electrode, the reference solution described above can also be used as the filling solution of the outer chamber of the reference electrode.

In the case of redox based reference system, such as the iodide/iodine Ross® system, cross-linking to form gel may be difficult due to quenching of the chain reaction by the redox species, therefore the electrolyte is instead thickened, e.g., with short chain cellulose, in order to create a low maintenance electrode. Among the polymer materials, polyacrylamides and celluloses are desirable for their inertness with the redox species and their ability to hold electrolyte solutions so as to thereby reduce water evaporation and salt creeping.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
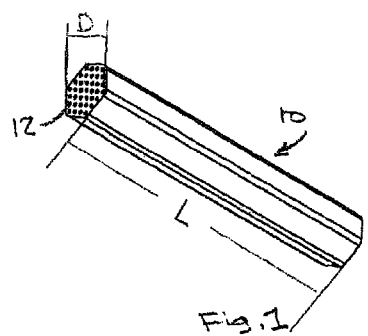
FIG. 1 is a view in perspective of one embodiment of multi-capillary junction in accordance with the invention.

In FIG. 1, capillary junction 10 of glass, e.g., borosilicate or quartz, has a multiplicity of micron-sized holes or capillaries 12 extending lengthwise through it. The length L of the junction is approximately 0.4 inches, its width from face to face approximately 1/16th inch. The inside diameter of the capillaries 12 is of the order of from 1 to 150 microns. In the example shown, there are 37 such capillaries.

Figure 2:
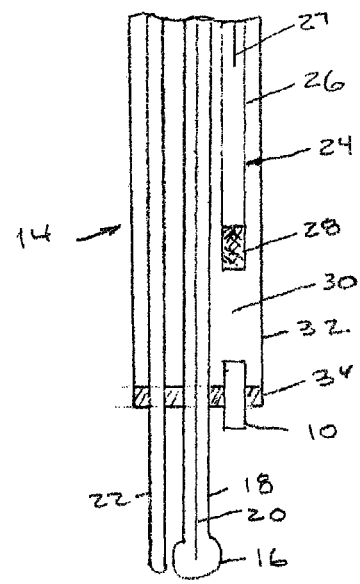
FIG. 2 is a sketch of a double junction pH electrode utilizing the multi-capillary junction of FIG. 1.

FIG. 2 illustrates the use of the junction of the present invention as a reference junction for an ion-selective electrode. In particular, there is shown in schematic form the lower end of a double junction pH electrode 14. The electrode 14 has a pH sensitive bulbous head 16 extending from a tube 18 in which an electrical lead wire 20 is contained. A thermistor 22 is positioned adjacent the head 16. An internal reference electrode 24 has tubing 26 terminated in a porous plug 28. The tubing 26 encloses an electrically conductive wire 27 and is filled with a first reference solution (not shown) which permeates through the plug 28 into a chamber 30 confined by outer wall 32 of the electrode 14. This establishes a first stable reference potential for the sensing electrode. A second internal filling solution (not shown) is contained in the chamber 30. The bottom of this chamber is sealed fluid tight by a plug 34 through which the reference junction 10 of the present invention extends, as do the pH electrode 18 and thermistor 22. Junction 10 establishes a second stable reference potential for the sensing electrode. The first and second reference solutions may each be a mixture of an iodide/iodine electrolyte couple (e.g., a Ross® solution); a mixture of an iodide/iodine electrolyte and potassium chloride electrolytes; a mixture of potassium chloride electrolyte and potassium nitrate electrolytes, or a standard solution such as KCl, among others.

What is claimed is:

1. An electrochemical reference electrode comprising a multibore liquid junction body for controllably supplying an electrolyte to a test solution, said body including a multiplicity of micron-sized capillary channels extending therethrough along a length thereof for carrying said electrolyte therethrough, said body having a length measured along the channels which is greater than one times a width of the body as measured transverse to the channels.

2. An electrochemical reference electrode according to claim 1 in which in which said body is formed from a multiplicity of hollow-bore tubes, aligned in parallel with each other.

3. An electrochemical reference electrode according to claim 1 in which said body is a solid body of a length of from 10 to 10000 greater than its width.

4. An electrochemical reference electrode according to claim 2 in which the number of channels in said body is approximately from 10 to 1000.

5. An electrochemical reference electrode according to claim 3 in which the number of channels in said body is approximately from 10 to 1000.

6. An electrochemical reference electrode according to claim 2 in which the length of said body is from 0.1 to 1 inch.

7. An electrochemical reference electrode according to claim 3 in which the length of said body is from 0.1 to 1 inch.

8. An electrochemical reference electrode according to claim 2 in which the inner diameter of said channels is between 1 micron and 150 microns.

9. An electrochemical reference electrode according to claim 3 in which the inner diameter of said channels is between 1 micron and 150 microns.

10. An electrochemical reference electrode according to claim 2 in which said tubes are of glass.

11. An electrochemical reference electrode according to claim 1, additionally comprising a chamber through which the body extends, and additionally comprising a reference solution in the chamber that has been thickened by a viscosity-increasing agent or gelled so as to limit flow of the reference solution out of the chamber and into the test solution.

12. An electrochemical reference electrode according to claim 1, additionally comprising a chamber, the body extending through a lower end of the chamber to a position above the lower end of the chamber.

* * * * *